United States Patent
Reckziegel et al.

(10) Patent No.: US 7,129,380 B2
(45) Date of Patent: Oct. 31, 2006

(54) (Z)-7-CYCLOHEXADECEN-1-ONE AS AN ODORANT

(75) Inventors: Aurelia Reckziegel, Holzminden (DE); Ingo Wöhrle, Holzminden (DE); Steffen Sonnenberg, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 11/016,896

(22) Filed: Dec. 21, 2004

(65) Prior Publication Data

US 2005/0137120 A1    Jun. 23, 2005

(30) Foreign Application Priority Data

Dec. 23, 2003    (DE) ................................ 103 61 524

(51) Int. Cl.
*C07C 49/00*    (2006.01)
*C07C 45/00*    (2006.01)
*A61K 7/46*    (2006.01)

(52) U.S. Cl. ...................... 568/375; 568/350; 512/27

(58) Field of Classification Search ................. None
See application file for complete search history.

(56) References Cited

U.S. PATENT DOCUMENTS 2,790,005 A      4/1957   Blomquist
6,815,413 B1 *  11/2004   Eh et al. ...................... 512/27

OTHER PUBLICATIONS

H.H. Mathur, Macrocyclic Musk Compounts-IX* New Syntheses of Cyclohexadecenone and Cyclohexadecanone From Aleuritic Acid, Tetrahedron, 1965, vol. 21, pp. 1537-to 1540,Pergamon Press Ltd.

* cited by examiner

*Primary Examiner*—Sikarl A. Witherspoon
(74) *Attorney, Agent, or Firm*—Roylance, Abrams, Berdo & Goodman, L.L.P.

(57) ABSTRACT

The compound (Z)-7-cyclohexadecen-1-one is described as a musk odorant. Also described are odorant or aroma mixtures comprising (Z)-7-cyclohexadecen-1-one and one or more other odorants or aromas.

16 Claims, No Drawings

(Z)-7-CYCLOHEXADECEN-1-ONE AS AN ODORANT

CROSS-REFERENCE TO RELATED APPLICATION

This application claims the benefit under 35 U.S.C. § 119 of German Patent Application No. 103 61 524.5, filed 23 Dec. 2003, which is hereby incorporated by reference in its entirety.

FIELD OF THE INVENTION

This invention relates primarily to the novel compound (Z)-7-cyclohexadecen-1-one, odorant and aroma mixtures comprising (E,Z)-7-cyclohexadecen-1-one, the use thereof as an odorant or aroma (mixture), products perfumed therewith, and to methods for the preparation of 7-cyclohexadecen-1-one.

In the perfume industry there is generally a demand for musk odorants because of the continuing need to make new and modern fragrances with a musk scent available to consumers. Odorants with a musk odor are used in large quantities and innumerable variations in perfumes, odorant mixtures (perfume compositions) and fragrances for a wide variety of uses. Because of increasing consumer demand for new modern fragrance notes, there is a constant need in the perfume industry for odorants with which novel effects can be obtained in perfumes and new fashion trends thereby created. Compounds with a musk odor have always been important and much sought-after ingredients in the fragrance industry.

Musk odorants are therefore used today in many perfume compositions.

Typical macrocyclic musk odorants are characterized by a ring with from 13 to 17 carbon atoms and a ketone or ester as the functional group. Classic musk odorants are for example civetone, muscone, cyclopentadecanolide, ethylene brassylate and cyclopentadecanone. Perfumers generally speak of a "macromusk odor" when referring to these musk materials, some of these individual compounds differing very markedly from one another in their individual notes and aspects.

For the creation of novel modern compositions there is a constant demand for musk odorants with particular odor properties that are suitable as a base for the composition of novel modern perfumes with a complex musk character. As well as the typical musk odor, desirable musk odorants must also have other notes and aspects that give them an olfactory character and complexity.

The search for suitable musk odorants leading to the present invention was made more difficult by the following factors:

The mechanisms of olfactory perception are not sufficiently well understood;

The relationship between specific olfactory perception on the one hand and the chemical structure of the corresponding odorant on the other has not been adequately studied;

Even minor changes in the structure of a known odorant often cause a pronounced change in its sensory properties and adversely affect its tolerance by the human body.

The success of a search for suitable musk odorants is therefore highly dependent on the searcher's intuition.

It was therefore the object of the present invention to find macrocyclic musk compounds having new odor properties with which special odor notes and aspects could be imparted to perfume compositions.

It has now been found surprisingly that this object can be achieved with (Z)-7-cyclohexadecen-1-one.

In J. Am. Chem. Soc., 1955, 77, 5423 and U.S. Pat. No. 2,790,005 there was obtained from 1,9-cyclohexadecanedione by partial reduction and subsequent dehydration a mixture of (E,Z)-8-cyclohexadecen-1-one which had an "intense musk odor".

J. Chem. Soc. 1965, 6679 describes the synthesis of pure (Z)-8-cyclohexadecen-1-one by hydrogenation of 8-cyclohexadecyn-1-one. (Z)-8-cyclohexadecen-1-one is described as a "rather heavy musk".

DE 2 111 753 and J. Org. Chem., 1972, 37, 3846 describe macrocyclic compounds and methods for their preparation. It stated quite generally that these macrocyclic compounds have a "musk fragrance" which is usually regarded as an animalistic note in perfumes. A method is described for preparing (E,Z)-8-cyclohexadecen-1-one from 1,9-cyclohexadecadiene by mono-epoxidation, reduction and oxidation. However, no detailed odor description is given.

The synthesis of a mixture of (E)-7-cyclohexadecen-1-one and (E)-8-cyclohexadecen-1-one is described in Tetrahedron, 1965, 21, 1537. Aleuritic acid (9,10,16-trihydroxypalmitic acid) is protected as the isopropylidene derivative, oxidized to the dicarboxylic acid, hydrobrominated and esterified. From the resulting diester there is obtained in subsequent steps after bromine elimination a mixture of (E)-7-cyclohexadecen-1-one and (E)-8-cyclohexadecen-1-one. Because the authors were of the general opinion that the musk odor of cyclohexadecenones is not affected by the position of the double bond, they were not interested in isolating and characterizing the two individual isomers.

A mixture consisting of (E,Z)-8-cyclohexadecen-1-one has hitherto been on the market for a period of time under the name Animusk® (Fragrance Resources).

It has now been found surprisingly that (Z)-7-cyclohexadecen-1-one of formula (I) differs markedly in odor from (E)-7-cyclohexadecen-1-one and from the isomers of 8-cyclohexadecen-1-one.

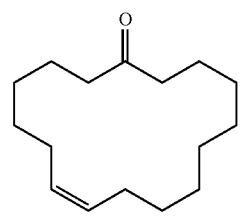

(Z)-7-Cyclohexadecen-1-one (I)

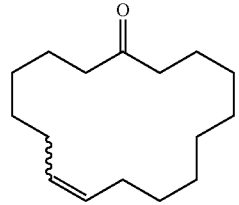

(E,Z)-7-Cyclohexadecen-1-one (II)

The odor description of individual isomers and mixtures of (E,Z)-7- and/or (E,Z)-8-cyclohexadecen-1-one is set out in Table 1.

TABLE 1

| Compound(s) | Odor description |
| --- | --- |
| (E)-7-Cyclohexadecen-1-one | Head note: strong musk odor, light nitro-musk note<br>Base note: on the whole rather weak, musk, somewhat erogenous, light nitro-musk note |
| (Z)-7-Cyclohexadecen-1-one<br>Formula (I) | Head note: the cleanest, most pure-toned and strongest musk odour of all the isomers and mixtures investigated here; crystalline and erogenous, slightly animalistic (civetone-like)<br>Base note: the most intense and typical musk odour of all the isomers; warm and erogenous, with crystalline and gentle animalistic notes. |
| (E,Z)-7-Cyclohexadecen-1-one | Head note: strong, clean musk note, crystalline nitro-musk note, slightly woody aspect<br>Base note: warm, erogenous, animalistic, crystalline, light nuances |
| (E)-8-Cyclohexadecen-1-one | Head note: strong musk odour, nitro-musk note<br>Base note: elegant, classic macromusk material, nitro-musk, clean, rather linear |
| (Z)-8-Cyclohexadecen-1-one | Head and base notes: similar to (E)-8-cyclohexadecen-1-one but on the whole slightly weaker, but with animalistic (muscone-like) nuances |
| (E,Z)-8-Cyclohexadecen-1-one | Head note: elegant, strong musk odour with a powerful nitro-musk note<br>Base note: elegant, classic macromusk material, nitro-musk, balsamic, clean, rather linear |
| Mixture of (E,Z)-7- and (E,Z)-8-Cyclohexadecen-1-one | Head note: powerful, clean and complex musk odour, pronounced nitro-musk note, fine flowery, sweet and powdery aspect, slightly woody accent<br>Base note: clean, complex, strong und exalting macromusk odour, warm, slightly crystalline, erogenous, animalistic, very natural and rounded, slightly woody nuance |

The mixtures that were subjected to odor evaluation had the following composition (values obtained from GC analysis):

(E,Z)-7-Cyclohexadecen-1-one of formula (II) contained 77.7% of (E)-7-cyclohexadecen-1-one and 21.8% of (Z)-7-cyclohexadecen-1-one of formula (I).

(E,Z)-8-cyclohexadecen-1-one contained 71.5% of (E)-8-cyclohexadecen-1-one and 28% of (Z)-8-cyclohexadecen-1-one.

The mixture of (E,Z)-7 and (E,Z)-8-cyclohexadecen-1-one was shown by GC analysis to contain 19.8% of (E)-7-cyclohexadecen-1-one, 8.4% of (Z)-7-cyclohexadecen-1-one of formula (I), 40.6% of (E)-8-cyclohexadecen-1-one and 30.5% of (Z)-8-cyclohexadecen-1-one (cf. Example 1.2 herebelow).

The pure isomers (E)-8-cyclohexadecen-1-one and (Z)-8-cyclohexadecen-1-one were obtained by Spaltrohr distillation from (E,Z)-8-cyclohexadecen-1-one.

The extensive sensory studies presented herein showed that the rather general information about the sensory evaluation of hitherto known 7/8-cyclohexadecenones that appears in the literature is insufficiently accurate or incorrect.

Surprisingly, the hitherto unknown (Z)-7-cyclohexadecen-1-one differs in olfactory terms very markedly from (E)-7-cyclohexadecen-1-one and from the isomers of 8-cyclohexadecen-1-one, in particular in its valuable crystalline nitro-musk note that is much sought-after by perfumers, and its clean, pure-toned and intense musk odor.

"Crystalline" is understood herein to mean the typical nitro-musk odor of musk ambrette (2,6-dinitro-3-methoxy-1-methyl-4-tert.-butylbenzene) which is characterized by a sweet, flowery and powdery musk odor.

Of the compounds that were investigated, (Z)-7-cyclohexadecen-1-one has the strongest and cleanest musk odor, in particular a nitro-musk odor that is similar to musk ambrette.

The combination of (Z)-7-cyclohexadecen-1-one (I) and (E)-7-cyclohexadecen-1-one in (E,Z)-7-cyclohexadecen-1-one (II) has a more complex musk odor than the individual isomers, more specifically the sought-after crystalline nitro-musk odor, together with a woody aspect. Preferred weight ratios of (E)-7-cyclohexadecen-1-one to (Z)-7-cyclohexadecen-1-one are in the range from 6:1 to 1:2 and more preferably they are in the range from 4:1 to 1:1.

The combination of (Z)-7-cyclohexadecen-1-one (I) and (E)-7-cyclohexadecen-1-one with (E,Z)-8-cyclohexadecen-1-one results in quite special odor effects. Advantageous weight ratios of (E,Z)-7-cyclohexadecen-1-one to (E,Z)-8-cyclohexadecen-1-one in the (E,Z)-7,8-cyclohexadecen-1-one mixture are in the range from 10:1 to 1:10, preferably in the range from 5:1 to 1:5 and more preferably in the range from 2:1 to 1:4.

The (E,Z)-7,8-cyclohexadecen-1-one mixture has, by comparison with a mixture of the pure trans-isomers (E)-7,8-cyclohexadecen-1-one, a markedly greater intensity, complexity, crystallinity and elegance and is therefore especially suitable for use in new and modern perfume compositions.

The (E,Z)-7,8-cyclohexadecen-1-one mixture has the greatest complexity of the mixtures that were investigated here and is characterized by its naturalness and radiance. The slightly woody accent harmonizes exceptionally well with the crystalline, exalting musk odor. In direct comparison with (E,Z)-8-cyclohexadecen-1-one, (E,Z)-7,8-cyclohexadecen-1-one also has a markedly lower odor threshold.

In mixtures with other odorants, (Z)-7-cyclohexadecen-1-one of the invention used in small amounts can boost the intensity of a perfume mixture and round off the overall impression of the perfume composition and give it more radiance and naturalness. In larger amounts, the clean, powerful musk odor comes to the fore and is accompanied by the crystalline nitro-musk note. The effects obtained with (E,Z)-7,8-cyclohexadecenone are reminiscent of musk ambrette and the composition has an elegant, exalting and crystalline musk odor.

In summary, the following compounds and mixtures (in accordance with the invention) therefore have a surprising odor quality:

(Z)-7-cyclohexadecen-1-one;

Odorant or aroma mixtures comprising (Z)-7-cyclohexadecen-1-one and one or more other odorants or aromas for example:

Odorant or aroma mixtures comprising (Z)-7-cyclohexadecen-1-one and (E)-7-cyclohexadecen-1-one, the weight ratio of (E)-7-cyclohexadecen-1-one to (Z)-7-cyclohexadecen-1-one preferably lying in the range from 6:1 to 1:2 and preferably in the range from 4:1 to 1:1.

Odorant or aroma mixtures comprising:
(Z)-7-cyclohexadecen-1-one,
(E)-7-cyclohexadecen-1-one,
(Z)-8-cyclohexadecen-1-one, and
(E)-8-cyclohexadecen-1-one, the weight ratio of (E,Z)-7-cyclohexadecen-1-one to (E,Z)-8-cyclohexadecen-1-one preferably lying in the range from 10:1 to 1:10, more preferably in the range from 5:1 to 1:5 and still more preferably in the range from 2:1 to 1:4.

There are preferred odorant or aroma mixtures in accordance with the invention (as characterized hereabove) in which the ratio of (E)-7-cyclohexadecen-1-one to (Z)-7-cyclohexadecen-1-one is not more than 50:1 and preferably not more than 10:1, since otherwise the sensory character of the mixture will not meet requirements.

One aspect of the invention which is closely linked to the above discussion is the use of (Z)-7-cyclohexadecen-1-one or an odorant or aroma mixture comprising (Z)-7-cyclohexadecen-1-one (as characterized hereabove) as a musk odorant or aroma or as a musk odorant or aroma mixture.

In a corresponding method of the invention for delivering, enhancing or modifying a musk odor, a sensorily active quantity of (Z)-7-cyclohexadecen-1-one or of an odorant or aroma mixture comprising (Z)-7-cyclohexadecen-1-one (as characterized hereabove) is brought into contact or mixed with a product.

7-Cyclohexadecen-1-one can be advantageously prepared from the known 1,8-cyclo-hexadecanedione by partial reduction and subsequent acid dehydration (a mixture of 7-cyclohexadecen-1-one and 8-cyclohexadecen-1-one is obtained). 8-Cyclohexadecen-1-one can be similarly obtained from the known 1,9-cyclohexadecanedione. A mixture of 1,8/1,9-cyclohexadecanediones can also be used and this is advantageous particularly for the preparation of the (E,Z)-7,8-cyclohexaden-1-one mixture. 1,8/1,9-cyclohexadecanediones are known for example from J. Org. Chem. 1968, 33, 4541 and U.S. Pat. No. 3,935,270.

The product of the partial reduction of 1,8 and/or 1,9-cyclohexadecanedione is a mixture containing unreacted diketone of formula (S1a), the required hydroxyketone of formula (S1b), and the diol of formula (S1c).

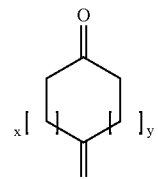

S1a

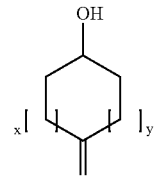

S1b

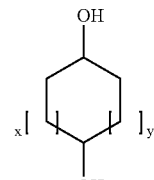

S1c

In the formulae, depending on the starting material, (a) x and y=6, or (b) x=5 and y=7.

The partial reduction of 1,8 and/or 1,9-cyclohexadecanedione can be carried out for example by reaction with metal hydrides or by means of hydrogenation.

The reaction with metal hydrides can for example be carried out with boron hydrides, preferably sodium borohydride, or with aluminum hydrides, preferably lithium aluminum hydride or diisobutyl aluminum hydride. Advantageously, 0.30–0.75 molar equivalents, calculated on the quantity of cyclohexadecanedione, are used. In the case of boron hydrides, the reaction is preferably carried out in optionally aqueous, protic solvents such as for example ethanol, methanol or isopropanol. In the case of aluminum hydrides, the reaction is preferably carried out in aprotic solvents such as for example diethyl ether, tetrahydrofuran or toluene.

For the hydrogenation, catalytic hydrogenation with hydrogen is preferred and is generally carried out in the presence of a hydrogenation catalyst from the group VII of the periodic table, such as for example palladium, nickel or platinum. The hydrogenation catalysts in accordance with the invention can be supported on organic or inorganic carrier materials.

The hydrogenation catalysts can contain one carrier material or mixtures of carrier materials. As advantageous carrier materials there can be mentioned activated carbon, carbon, aluminum oxides, metal oxides, silica gels, zeolites, clays, granular clays or amorphous aluminum silicates. Preferred catalysts are palladium on activated carbon, Raney nickel or platinum black. Hydrogenation can be carried out in solvents such as for example ethanol, isopropanol, ethyl acetate, hexane, cyclohexane, or it can be carried out without solvents, in other words it can be a bulk reaction. Typically, hydrogenation is carried out at a hydrogen pressure in the range from 1 to 100 bar, the temperature is usually in the range from 20 to 150° C. The weight ratio of the hydrogenation catalyst used to the 1,8 and/or 1,9-cyclohexanedecanedione is usually in the range from 0.00001:1 to 0.1:1.

Because incomplete hydrogenation is necessary for the required hydroxyketones of formula (S1b) to be formed, a 20–70% theoretical uptake of hydrogen, calculated on the 1,8 and/or 1,9-cyclohexadecanedione is preferred, so that complete hydrogenation of the two ketone groups does not take place.

Especially preferred is catalytic hydrogenation in the presence of Raney nickel as the hydrogenation catalyst, optionally in the presence of catalytic amounts (usually from 0.05 to 5% by weight, on the 1,8 and/or 1,9-cyclohexadecanedione) of bases such as alkali metal hydroxides, for example sodium hydroxide, or alkali metal alcoholates, for example sodium methanolate. Preferably, the hydrogenation is carried out at a hydrogen pressure in the range from 1 to 50 bar and preferably from 10 to 20 bar. The temperature during hydrogenation is typically in the range from 20 to 100° C., and preferably in the range from 50 to 80° C.

A theoretical hydrogen uptake of 30–60% is preferred, calculated on the 1,8 and/or 1,9-cyclohexadecanedione, and more preferably it is 35–55%. The weight ratio of the hydrogenation catalyst used to 1,8 and/or 1,9-cyclohexadecanedione can be between 0.0001:1 and 0.1:1, and a ratio of from 0.001:1 to 0.05:1 is preferred. The reaction time for the hydrogenation is advantageously from 1 to 50 hours and preferably it is from 6 to 15 hours. The GC content (content obtained in the gas-chromatogram) of the desired hydroxyketones of formula (S1b) in the crude hydrogenation product is usually in the range from 40 to 70%.

The crude hydrogenation product which essentially consists of compounds (S1a), (S1b) and (S1c) can be used in the elimination (dehydration) reaction without further cleanup.

However, if necessary, the crude product can be cleaned up by the usual methods (distillation, chromatography, as well as crystallization) and the purified hydroxyketone of formula (S1b) can be used in subsequent dehydration step.

In a second step, the hydroxyketones of formula (S1b) are dehydrated under acid conditions by methods that are well-known to the person skilled in the art. Suitable acid catalysts are for example concentrated sulphuric acid, p-toluenesulphonic acid, benzenesulphonic acid and acid ion-exchangers (for example from the range of commercially available Lewatites® or Amberlites®).

After dehydration of the crude product obtained from the hydrogenation of 1,8 and/or 1,9-cyclohexadecanedione, the resulting mixture consists essentially of the following products:

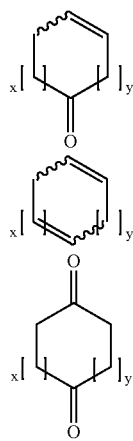

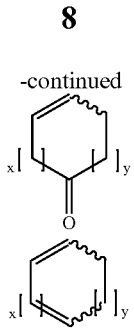

Here again, depending on the starting material, x and y=6 or x=5 and y=7.

Starting with pure 1,9-cyclohexadecanedione, partial reduction and dehydration yield 1,9-cyclohexadecanedione, (E,Z)-8-cyclohexadecenone, 1,8-cyclohexadecadiene and 1,9-cylcohexadecadiene.

Starting with pure 1,8-cyclohexadecanedione, partial reduction and elimination yield 1,8-cyclohexadecanedione, (E,Z)-7-cyclohexadecenone, (E,Z)-8-cyclohexadecenone, 1,7-cyclohexadecadiene, 1,8-cyclohexadecadiene and 1,9-cyclohexadecadiene.

Thus, starting with a mixture of 1,8 and 1,9-cyclohexadecanedione (GC analysis showed the ratio to be about 1:1) there was obtained after partial reduction and subsequent dehydration a product in which (E,Z)-7-cyclohexadecen-1-one and (E,Z)-8-cyclohexadecen-1-one were present in a ratio of about 3:7.

In addition, an alternative method was developed for the preparation of the (E,Z)-7-cyclohexadecen-1-one of formula (II) in accordance with the invention, comprising the following steps:

(a) condensing 7-octenecarboxylic acid with N,O-dimethylhydroxylamine to the methoxymethyl amide of oct-7-enoic acid, (b) converting 1-bromo-9-decene into the corresponding Grignard compound, (c) Reacting the methoxymethyl amide of oct-7-enoic acid with the Grignard compound to give 1,17-octadecadien-8-one, and (d) converting 1,17-octadecadien-8-one by ring-closing olefin metathesis into (E,Z)-7-cyclohexadecenone.

In a first step, condensation of 7-octenecarboxylic acid [J. Org. Chem., 1968, 33, 1550–1556] with N,O-dimethylhydroxylamine furnishes the methoxymethyl amide of oct-7-enoic acid (Weinreb amide) [Synthesis, 2000, 1852–1862].

Thereafter, 1-bromo-9-decene converted into the corresponding Grignard compound is reacted with the above Weinreb amide to give 1,17-octadecadien-8-one.

The (E,Z)-7-cyclohexadecen-1-one (II) of the invention is then prepared from the α,ω-unsaturated diene 1,17-octadecadien-8-one in a ring-closing olefin metathesis. For example, 1,17-octadecadien-8-one is reacted as a 0.01–0.001 molar solution in the presence of from 0.5 to 10 mol-% of a metathesis catalyst based on Mo, W, or Ru. Advantageously, the reaction is carried out in the presence of benzylidene-bis-(tricyclohexylphosphine)-dichlororuthenium (Grubbs catalyst) [Synthesis, 1977, 792; Synlett, 1997, 1010].

The method of the invention can be described by the following formulae

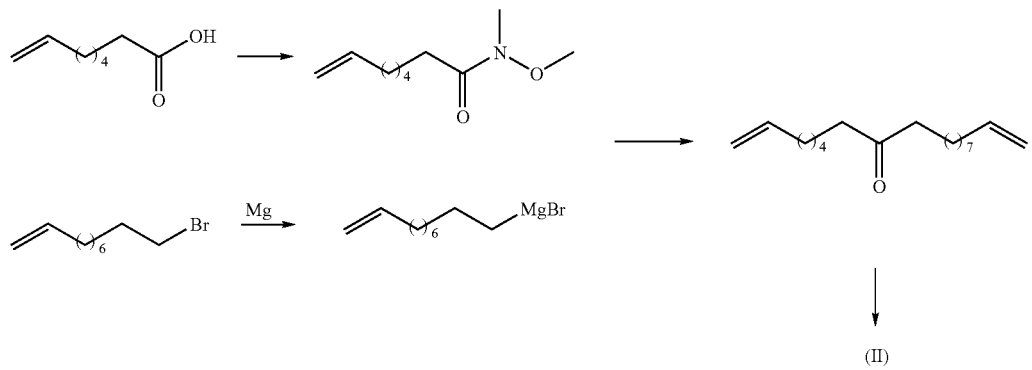

The invention also relates to perfumed products comprising (Z)-7-cyclohexadecen-1-one or an odorant or aroma mixture containing (Z)-7-cyclohexadecen-1-one (as characterized hereabove).

Other conventional perfume components with which (Z)-7-cyclohexadecen-1-one, (E,Z)-7-cyclohexadecen-1-one or (E,Z)-7,8-cyclohexadecen-1-one can be advantageously combined are listed for example in Steffen Arctander, Perfume and Flavor Chemicals, private publication, Montclair, N.J., 1969; K. Bauer, D. Garbe, H. Surburg, Common Fragrance and Flavor Materials, 4$^{th}$ Edition, Wiley-VCH, Weinheim 2001.

In particular, there can be mentioned:

Extracts of natural raw materials such as essential oils, concretes, absolutes, resins, resinoids, balsams, tinctures such as for example ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco-leaf oil; cabreuva oil; cade oil; calamus oil; camphor oil; cananga oil; cardamom oil; cascarilla oil; cassia oil; cassia absolute; castoreum absolute; cedar-leaf oil; cedarwood oil; cistus oil; citronella oil; lemon oil; copaiba balsam; copaiba balsam oil; coriander oil; costus_ root oil; cumin oil; cypress oil; davana oil; dill oil; dillseed oil; eau de brouts absolute; oakmoss absolute; elemi oil; tarragon oil; eucalyptus citriodora oil; eucalyptus oil; fennel oil; fir oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue chamomile oil; Roman chamomile oil; carrot-seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; Litsea cubeba oil; bay-leaf oil; mace oil; marjoram oil; mandarin oil; massoia bark oil; mimosa absolute; ambrette oil; tincture of musk; clary sage oil; myristica oil; myrrh absolute; myrrh oil; myrtle oil; clove leaf oil; clove flower oil; neroli oil; olibanum abolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; Japanese aniseed oil; styrax oil; tagetes oil; fir-needle oil; tea-tree oil; turpentine oil; thyme oil; Tolu balsam; tonka absolute; tuberose absolute; vanilla extract; violet leaf absolute; verbena oil; vetiver oil; juniper oil; wine-lees oil; wormwood oil; wintergreen oil; ylang oil; hyssop oil; civet absolute; cinnamon leaf oil; cinnamon bark oil; as well as fractions thereof or constituents isolated therefrom;

Individual odorants from the group of hydrocarbons, such as for example 3-carene; α-pinene; β-pinene; α-terpinene; γ-terpinene; p-cymene; bisabolene; camphene; caryophyllene, cedrene; farnesene; liminene; longifolene; myrcene; ocimene; valencene; (E,Z)-1,3,5-undecatriene;

Aliphatic alcohols such as for example hexanol; octanol; 3-octanol; 2,6-dimethylheptanol; 2-methylheptanol; 2-methyloctanol; (E)-3-hexenol; (E) and (Z)-3-hexenol; 1-octen-3-ol; mixtures of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their 1,4-dioxacycloalken-2-ones such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

Aliphatic ketones and oximes thereof such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; aliphatic sulphur-containing compounds such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

Aliphatic nitriles such as for example 2-nonenenitrile; 2-tridecenenenitrile; 2,12-tridecenene-nitrile; 3,7-dimethyl-2,6-octadienenitrile; 3,7-dimethyl-6-octenenitrile;

Aliphatic carboxylic acids and esters thereof, such as for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl-2-isoamyloxyacetate; methyl-3,7-dimethyl-2,6-octadienoate;

Acyclic terpene alcohols such as for example citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

Acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

Cyclic terpene alcohols such as for example menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates thereof;

Cyclic terpene aldehydes and ketones such as for example menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

Cyclic alcohols such as for example 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

Cycloaliphatic alcohols such as for example alpha-3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers such as for example cineol; cedryl methyl ether; cyclododecyl methyl ether; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydro-naphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

Cyclic ketones such as for example 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

Cycloaliphatic aldehydes such as for example 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones such as for example 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl (2,4-dimethyl-3-cyclohexen-1-yl) ketone;

Esters of cyclic alcohols such as for example 2-tert.-butylcyclohexyl acetate; 4-tert.-butyl-cyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

Esters of cycloaliphatic carboxylic acids such as for example, allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic hydrocarbons such as for example styrene and diphenylmethane;

Araliphatic alcohols such as for example benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers such as for example 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes such as for example benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal;

cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxy-benzaldehyde; 2-methyl-3-(4-methoxyphenyl)propanal; 2-methyl-3-(4-methylenedioxyphenyl)propanal;

Aromatic and araliphatic ketones such as for example acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

Aromatic and araliphatic carboxylic acids and esters thereof such as for example benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

Nitrogen-containing aromatic compounds such as for example 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert.-butylphenyl)propanal or 2,4-dimethyl-3-cyclohexene-carbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine;

Phenols, phenyl ethers and phenyl esters such as for example estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

Heterocyclic compounds such as for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

Lactones such as for example 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis and trans-11-pentadecen-1,15-olide; cis and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Perfume oils containing the (E,Z)-7,8-cyclohexadecenone, (E,Z)-7-cyclohexadecenone or (Z)-7-cyclohexadecenone of the invention can be used for fragrance purposes in a liquid form, undiluted or diluted in a solvent. Useful solvents are for example ethanol, isopropanol, diethylene glycol monoethyl ether, glycerol, propylene glycol, 1,2-butylene glycol, dipropylene glycol, diethyl phthalate, triethyl citrate, isopropyl myristate and the like.

It is advantageous in many applications for perfume oils containing (E,Z)-7,8-cyclohexadecenone, (E,Z)-7-cyclohexadecenone or (Z)-7-cyclohexadecenone to be adsorbed onto a carrier substance which provides both for the fine distribution of the odorants in the product and their controlled release during use. Such carriers can be porous inorganic materials such as light sulphate, silica gels, zeolites, gypsums, clays, granular clay, gas concrete and the like, or organic materials such as woods, cellulose-based materials, sugars or plastics such as PVC, polyvinyl acetates or polyurethanes.

For other applications, it is advantageous for perfume oils containing (E,Z)-7,8-cyclohexadecenone, (E,Z)-7-cyclohexadecenone or (Z)-7-cyclohexadecenone to be microencapsulated, spray-dried, in the form of an inclusion complex or an extrusion product and for them to be added in this form to the (starting) product that is to be fragranced.

The properties of perfume oils that have been modified in this manner are sometimes optimized still further to provide a more targeted fragrance release by coating them with suitable materials, waxy plastics such as for example polyvinyl alcohol being preferably used.

Perfume oils can be microencapsulated for example by the coacervation method using capsule materials consisting for example of polyurethane-like materials or soft gelatin. Spray-dried perfume oils can for example be obtained by spray-drying an emulsion or dispersion that contains the perfume oil, for which purpose modified starches, proteins, dextrin and plant gums can be used as carrier materials. Inclusion complexes can be prepared for example by introducing dispersions of the perfume oil and cyclodextrins or urea derivatives into a suitable solvent, for example water. Extrusion products can be obtained by melting perfume oils together with a suitable waxy material followed by extrusion and subsequent hardening, optionally in a suitable solvent, for example isopropanol.

Perfume oils containing the compounds of the invention, (E,Z)-7,8-cyclohexadecenone, (E,Z)-7-cyclohexadecenone or (Z)-7-cyclohexadecenone, can be used in concentrated form, in solution or in any modified form for the preparation of for example perfume extracts, eaux de parfum, eaux de toilette, shaving lotions, eaux de cologne, pre-shave products, splash colognes and perfumed wipes, as well as for adding fragrances to acidic, alkaline or neutral cleaning products such as for example floor cleaners, window cleaners, dishwashing detergents, bath cleaners and sanitizers, abrasive creams, solid and liquid toilet cleaners, powdered and mousse carpet cleaners, liquid detergents, powder detergents, laundry pre-treatment products such as bleaches, soaking products and stain removers, fabric conditioners, laundry soaps, laundry tablets, disinfectants, hard surface disinfectants as well as air improvers in liquid or gel form or applied to a solid carrier, aerosol sprays, waxes and polishes such as furniture polishes, floor waxes, shoe creams as well as toiletries and personal care formulation such as, for example, solid and liquid soaps, shower gels, shampoos, shaving soaps, shaving foams, bath oils, cosmetic emulsions of the oil-in-water, water-in-oil, and water-in-oil-in-water type, such as for example skin creams and lotions, face creams and lotions, sun-protection creams and lotions, aftersum creams and lotions, hand creams and lotions, foot creams and lotions, depilatory creams and lotions, aftershave creams and lotions, tanning creams and lotions, haircare products such as for example hairsprays, hair gels, hair lotions, hair conditioners, permanent and semi-permanent hair dyes, hair-shaping products such as cold waving and hair-straightening products, hair tonics, hair creams and lotions, deodorants and antiperspirants such as for example underarm sprays, roll-ons, stick deodorants, cream deodorants, or decorative cosmetic products.

In perfume oil compositions (=odorant mixtures), the amount of (Z)-7-cyclohexadecenone used is usually in the range from 0.001 to 70% by weight, preferably from 0.05 to 50% by weight and more preferably from 0.5 to 25% by weight, calculated on the total perfume oil composition.

In perfume oil compositions, the amount of (E,Z)-7-cyclohexadecenone or (E,Z)-7,8-cyclohexadecenone used is usually in the range from 0.01 to 90% by weight, preferably from 0.1 to 70% by weight and more preferably from 1 to 40% by weight, calculated on the total perfume oil composition.

Additives with which the materials of the invention can be combined are for example:

Preservatives, abrasives, anti-acne agents, anti-skin ageing agents, antibacterial agents, anticellulite agents, anti-dandruff agents, anti-inflammatory agents, irritation-preventing or inhibiting agents, antimicrobial agents, antioxidants, astringents, antiperspirants, antiseptics, antistatics, binders, buffers, carriers, chelating agents, cell stimulants, cleaning agents, caring agents, depilatories, surface-active agents, deodorants, antiperspirants, softeners, emulsifiers, enzymes, essential oils, fibres, film-formers, fixatives, foaming agents, foam stabilizers, foam-suppressors, foam boosters, fungicides, gelling agents, gel-forming agents, hair-care agents, hair-shaping agents, hair-straightening agents, moisturizing agents, wetting agents, humectants, bleaching agents, starching agents, stain-removing agents, optical brighteners, water-proofing agents, soil-repelling agents, friction-reducing agents, lubricants, moisture creams, ointments, clouding agents, plasticizers, opacifiers, polishes, glossing agents, polymers, powders, proteins, refatting agents, exfoliating agents, silicones, skin-soothing agents, skin-cleansing agents, skin-care agents, skin-healing agents, skin-lightening agents, skin-protecting agents, skin softening agents, cooling agents, skin-cooling agents, heating agents, skin-heating agents, stabilizers, UV-absorbing agents, UV-filters, laundry detergents, fabric softeners, suspending agents, skin-tanning agents, thickeners, vitamins, oils, waxes, fats, phospholipids, saturated fatty acids, monounsaturated or polyunsaturated fatty acids, $\alpha$-hydroxy acids, polyhydroxy fatty acids, liquefying agents, dyes, color-protection agents, pigments, anti-corrosives, flavors, flavoring materials, odorous materials, polyols, surfactants, electrolytes, organic solvents or silicone derivatives.

(E,Z)-7,8-Cyclohexadecenone, (E,Z)-7-cyclohexadecenone and (Z)-7-cyclohexadecenone can be used together with other musk odorants to produce further combinations and effects of olfactory interest; even more highly-facetted musk notes can be obtained particularly in combination with macrocyclic ketones and in particular lactones having a musk odor. Of the lactones, 1,15-cyclopentadecanolide, 11-pentadecen-15-olide, 12-pentadecen-15-olide, 1,16-hexadecanolide and ethylene brassylate or mixtures thereof are preferred. Of the ketones, muscone, civetone, muscenone, cyclopentadecanone and cyclohexadecanone are advantageous.

The (E,Z)-7,8-cyclohexadecenone, (E,Z)-7-cyclohexadecenone and (Z)-7-cyclohexadecenone compounds and mixtures in accordance with the invention, and odorant or aroma mixtures (as characterized hereabove) containing (E,Z)-7,8-cyclohexadecenone, (E,Z)-7-cyclo-hexadecenone and (Z)-7-cyclohexadecenone of the invention are characterized by good absorbtivity (adhesion to a substrate) and good substantivity (ability to be absorbed from a phase, usually an aqueous phase, onto a substrate, and to remain on a substrate after washing or rinsing). This effect is obtained in particular on substrates such as skin, hair, and textile fibres (for example wool, cotton, linen, synthetic fibres).

Consequently, especially preferred perfumed products in accordance with the invention are detergents, toiletry and care products, in particular in the field of personal care, cosmetics and the home.

Odorants that improve the tenacity of a composition (in other words that act as fixatives) or enhance the intensity of olfactory perception (in other words that act as boosters) are also of appreciable interest for perfume composition.

As well as having a high absorptivity, (Z)-7-cyclohexadecenone and the mixtures of the invention are also characterized by their fixative properties. A fixative of this kind increases the tenacity of other odorants, either by lowering their vapor pressure or by odor intensification (for example by lowering the threshold value). Accordingly therefore, the invention also relates to the use of (Z)-7-cyclohexadecen-1-one or an odorant or aroma mixture comprising (Z)-7-cyclohexadecen-1-one (as characterized hereabove) as a fixative.

Moreover, (Z)-7-cyclohexadecenone and the mixtures of the invention act not only as fixatives but also as boosters or enhancers, that is to say, they intensify the odor or the olfactory perception of odorants, odorant mixtures and perfume compositions. Accordingly therefore, the invention also relates to the use of (Z)-7-cyclohexadecen-1-one or an odorant mixture (as characterized hereabove) containing (Z)-7-cyclohexadecen-1-one as a means of enhancing the olfactory perception of odorants or odorant compositions.

The above-described effects of (Z)-7-cyclohexadecenone and of mixtures in accordance with the invention on odorant compositions are evident in particular from a comparison of the change in odor with time during use.

The following examples describe the invention; unless otherwise stated, all parts and percentages are by weight.

EXAMPLES

Example 1

Preparation of (E,Z)-7,8-cyclohexadecen-1-one

Example 1.1

3 mol (758 g) of a mixture of 1,8 and 1,9-cyclohexadecanedione (isomer ratio 1:1) was hydrogenated in 800 ml of isopropanol in the presence of 3% by weight of Raney nickel at a temperature of 80° C. and a hydrogen pressure of 10–20 bar. After an uptake of 40% of the theoretical amount of hydrogen, the hydrogenation was stopped, the reaction mixture was filtered off from the catalyst and the solvent removed. There was obtained 758 g of crude product having a composition (GC content) of 23% of 8-/9-dihydroxycyclohexadecane, 53% of 8-/9-hydroxycyclohexadecanone and 23% of 1,8-/1,9-cylcohexadecanedione. This crude product was used, without any clean-up, in the subsequent dehydration step.

Example 1.2

Into a 2-liter three-neck flask fitted with a stirrer, internal thermometer, water separator and a heating mantle there was charged the mixture obtained in Example 1.1 in 600 g of toluene and 20 g conc. sulphuric acid were added. The mixture was heated to boiling at the water separator with continuous stirring until no more water was formed (volume of water separated: about 62 ml). After cooling to room temperature, 250 g of water, 5 g of AcOH and 15 g of NaCl were added, stirred and the phases separated. The organic phase was neutralized by adding, with caution, 250 ml of saturated NaHCO₃ solution, the resulting mixture was heated to 70° C. for better phase separation, and thereafter a further 600 g of toluene were added and the phases were again separated. After the toluene had been removed, there was obtained 574 g of crude product having GC content of 22% of cyclohexdecadiene, 53% of (E,Z)-7,8-cylcohexadecen-1-one, and 22% of 1,8/1,9-cyclohexadecanedione. After distillation on a 7-plate Siegwart column there was obtained 252 g of (E,Z)-7,8-cyclohexdecen-1-one (B.P. 117–120° C., 0.4 bar), which had the following composition (GC): 19.8% (E)-7-cyclo-hexadecen-1-one, 8.4% (Z)-7-cyclohexadecen-1-one, 40.6% (E)-8-cyclohexadecen-1-one and 30.5% (Z)-8-cyclohexadecen-1-one.

$^1$H-NMR (400 MHz, CDCl₃): δ (ppm)=1.30–1.401 (m, 14H), 1.56–1.70 (m, 4H), 2.00–2.08 (m, 4H), 2.32–2.46 (m, 4H), 5.24–5.38 (m, 2H).

Example 2

(E,Z)-7-cyclohexadecen-1-one

1-Bromo-9-decene (10-bromo-dec-1-ene)

A solution of 20 g (0.14 mol) of triphenyl phosphine in 250 ml of dichloromethane was cooled to −10° C. in a nitrogen atmosphere. 22.53 g (0.14 mol) of bromine were then added dropwise with caution until the reaction mixture had just turned yellow in color. A few triphenyl phosphine crystals were then added with stirring until the yellow color had just disappeared. To the colourless suspension there were added 20 g (0.12 mol) of 10-decen-1-ol (source: SIGMA-ALDRICH), the cold bath was removed and stirring was continued at 20° C. for 2 hours. Thereafter 50 ml of saturated NaHCO₃ solution were added with caution and the mixture was diluted with 100 ml of cyclohexane. The phases were separated and the aqueous phase was extracted three times with 50-ml portions of cyclohexane. The combined organic phases were dried over sodium sulphate and concentrated. The residue was taken up in cyclohexane and cooled to 4° C. The precipitated triphenyl phosphine oxide was filtered off, the filtration residue was washed with a little cyclohexane and the filtrate was again concentrated. Column chromatographic fractionation of the resulting residue furnished 24 g (0.11 mol) of 1-bromo-9-decene as a paleyellow oil.

$^1$H-NMR (400 MHz, CDCl₃): δ (ppm)=1.30–1.46 (m, 10H), 1.82–1.89 (m, 2H), 2.00–2.08 (m, 2H), 3,405 (t, J=6, 87 Hz, 2H), 4.93 (ddt, J=10.1, 4.9, 2.23 Hz, 1H), 499 (ddt, 17.1, 4.9, 2.18 Hz, 1H), 5.8 (ddt, 17.1, 10.1, 6.56 Hz, 2H).
$^{13}$C-NMR (101 MHz, CDCl₃): δ (ppm)=28.16, 28.72, 28.87, 29.00, 29.27, 32.83, 33.77, 34.00, 114.19, 139.13.

Methoxymethyl Amide of 7-octenoic acid:

1.10 g (7.73 mmol) of 7-octenoic acid [J. Org. Chem., 1968, 33, 1550–1556] were dissolved in 35 ml of dichloromethane and cooled to 0° C. There were then added 1.75 ml (10.05 mmol) of ethyl-diisopropyl amine, 935 mg (9.6 mmol) of N,O-dimethylhydroxylamine hydrochloride and 1.63 g (8.50 mmol) of N,N-dicyclohexylcarbodiimide. Thereafter, the charge was cooled to 0° C. and a catalytic quantity of N,N-dimethylaminopyridine was added. The reaction mixture was stirred overnight at room temperature. The precipitated urea derivative was filtered off, and the filtrate was concentrated. The residue was taken up in pentane and any urea derivative that precipitated out was again filtered off. The organic phase was washed twice with 0.5M hydrochloric acid and once with saturated NaHCO₃ solution, dried and concentrated. Column-chromatographic fractionation furnished 1 g (5.41 mmol) of the methoxymethyl amide of oct-7-enoic acid.

$^1$H-NMR (400 MHz, CDCl₃): δ (ppm)=1.31–1.47 (m, 4H), 1.64 (q, J=7.46 Hz, 2H), 2.05 (dt, J=6.81, 1.38 Hz, 2H), 2.41 (t, 7.58 Hz, 2H), 3.17 (s, 3H), 3.68 (s, 3H), 4.93 (ddt, J=10.16, 2.1, 1.23 Hz, 1H), 4.99 (ddt, J=17.1, 2.1, 1.5 Hz, 1H), 5.80 (ddt, J=17.01, 10.1, 6.7 Hz, 1H).
$^{13}$C-NMR (101 MHz, CDCl₃): δ (ppm)=24.48, 28.70, 28.92, 31.86, 32.21, 33.63, 61.20, 114.32, 138.97, 174.69.

1,17-Octadecadien-8-one

A Grignard solution was prepared under nitrogen from 2.15 g (8.53 mmol) of 10-bromodec-1-ene and 249 mg (10.22 mmol) of magnesium powder in 20 mL of diethyl ether. The fresh Grignard solution was slowly added dropwise under a N₂ atmosphere at 0° C. to a solution of 790 mg (4.26 mmol) of the methoxymethyl amide of oct-7-enoic acid and 10 mL of diethyl ether. Stirring was then continued at 20° C. for one hour. The charge was carefully quenched with Na₄Cl solution and then extracted twice with diethyl ether. The organic phase was again washed with water, dried and concentrated. Column chromatographic fractionation furnished 820 mg (3.11 mmol) of octadeca-1,17-dien-8-one.

$^1$H-NMR (400 MHz, CDCl₃): δ (ppm)=1.25–1.44 (m, 14H), 1.53–1.61 (m, 4H), 2.0–2.08 (m, 4H), 2.37(t, J=7.4 Hz, 2H), 2.38 (t, J=7.4 Hz, 2H), 4.92 (ddt, J=10.2, 2.8, 1.2 Hz, 1H), 4.93 (ddt, J=10.2, 2.8, 1.2 Hz, 1H), 4.98 (ddt, J=17.1, 2.2, 1.6 Hz, 1H), 4.99 (ddt, J=17.1, 2.2, 1.6 Hz, 1H), 5.79 (ddt, J=17.1, 10.3, 6.7 Hz, 1H), 5.80 (ddt, J=17.1, 10.3, 6.7 Hz, 1H).
$^{13}$C-NMR (101 MHz, CDCl₃): δ (ppm)=23.71, 23.88, 28.69, 28.73, 28.92, 29.08, 29.26, 29.32, 29.37, 33.59, 33.80, 42.73, 42.83, 114.15, 114.38, 138.86, 139.17, 211.51.

(E,Z)-7-Cyclohexadecenone/isomer separation:

To a solution of 820 mg (3.11 mmol) of octadeca-1,17-dien-17-one in 560 ml of CH₂Cl₂ there were added 200 mg (0.243 mmol) of benzylidene-bis-(tricyclohexylphosphine)-dichlororuthenium (Grubbs catalyst) dissolved in 20 ml of CH₂Cl₂ and heated under reflux for 6–8 hours. After cooling to room temperature, the reaction solution was washed twice with 100-ml portions of 1 N hydrochloric acid, dried over Na₂SO₄, and filtered on a short silica gel column. After the solvent was removed, there was obtained 670 g of crude (E,Z)-7-cyclohexadecen-1-one (ratio of (E):(Z) isomers about 3:1).

300 mg (GC purity of about 95%) of the (E,Z)-7-cyclohexadecenone were separated by HPLC. There were obtained 170 mg of (E)-7-cyclohexadecenone with a GC purity of greater than 97% and 55 mg of (Z)-cyclohexadecenone with a GC purity of greater than 97%, and 50 mg of a (E,Z)-7-cyclohexadecenone mixed fraction.

HLPC conditions: Column: Saphir 110 Si, 5 μm, 125×20 mm, eluent: heptane/tert.-butyl methyl ether (v/v) 99:01, flow: 25 ml/min, pressure: 43 bar, temperature: 20° C., detection: IR; additional detection: UV at 285 nm.

(Z)-7-Cyclohexadecenone:

$^1$H-NMR (400 MHz, CDCl₃): δ (ppm)=1.24–1.40 (m, 14H), 1.54–1.70 (m, 4H), 1.99–2.07 (m, 4H), 2.39 (t, J=6.3 Hz, 2H), 2.41 (t, J=6.3 Hz, 2H), 5.26–5.38 (m, 2H).

$^{13}$C-NMR (101 MHz, CDCl$_3$): δ (ppm)=23.44, 24.43, 26.85, 27.00, 27.01, 27.68, 27.93, 28.06, 28.48, 28.68, 29.25, 41.78, 42.00, 130.07, 130.15, 212.36. IR (cm$^{-1}$): 2997, 2925, 2853, 1707, 1459, 1439, 1404, 1369, 1207, 844, 718.

(E)-7-Cyclohexadecenone:
$^1$H-NMR (400 MHz, CDCl$_3$): δ (ppm)=1.16–1.40 (m, 14H), 1.60–1.65 (m, 4H), 1.98–2.06 (m, 4H), 2.36–2.44 (m, 4H), 5.22–5.31 (m, 2H).
$^{13}$C-NMR (101 MHz, CDCl$_3$): δ (ppm)=23.71, 24.21, 26.53, 27.23, 27.77, 28.12, 28.29, 28.31, 29.10, 31.96, 32.48, 42.13, 42.59, 130.92, 131.08, 212.10. IR (cm$^{-1}$): 2981, 2925, 2851, 1709, 1457, 1433, 1363, 1262, 1210, 1164, 1132, 1103, 1052, 964.

Example 3

The following perfume oil is used in practical applications to perfume a wide variety of cosmetic products.

COMPOSITION

| Ingredients | Parts by weight |
| --- | --- |
| 1. Citrophoral Base (Symrise) | 5.0 |
| 2. Aldehyde C10 10% in BA | 5.0 |
| 3. Aldehyde C11 MOA 10% in BA | 3.0 |
| 4. Farenal (Symrise) | 3.0 |
| 5. Aldehyde C11 10% in IPM | 5.0 |
| 6. Citroxal 50% in DEP | 2.0 |
| 7. trans-Hex-2-enol 10% in BA | 2.0 |
| 8. Vertocitral (Symrise) | 1.0 |
| 9. Linalyl acetate | 45.0 |
| 10. Citrylal (Symrise) | 5.0 |
| 11. Mandarinal (Firmenich) | 4.0 |
| 12. Lilial (Givaudan Roure) | 75.0 |
| 13. Lyral (IFF) | 75.0 |
| 14. Profarnesol (Symrise) | 5.0 |
| 15. Nerolidol | 5.0 |
| 16. Linalool | 45.0 |
| 17. Geranium oil African | 5.0 |
| 18. Phenylethyl alcohol | 75.0 |
| 19. Geraniol | 15.0 |
| 20. Nerol | 10.0 |
| 21. Hexylcinnamaldehyde alpha | 50.0 |
| 22. Methyldihydrojasmonate | 15.0 |
| 23. Benzyl salicylate | 100.0 |
| 24. trans,cis-2-Nonadienol 0.1% in IPM | 5.0 |
| 25. Allyl ionone (Givaudan Roure) | 3.0 |
| 26. Isomethyl ionone gamma | 75.0 |
| 27. Eugenol | 7.0 |
| 28. Cedryl acetate | 40.0 |
| 29. Sandolen (Symrise) | 5.0 |
| 30. Citral | 5.0 |

BA=benzyl alcohol, IPM=isopropyl myristate, DEP=diethyl phthalate

The addition of a) 55 parts by weight of (E,Z)-7,8-cyclohexadecenone (composition as in Example 1.2: total perfume oil: 700 parts by weight) imparted to the composition a slightly erogenous, crystalline nitro-musk note which cannot be obtained with existing macrocyclic musk odorants. The whole composition gained in naturalness and radiance and was more rounded and more elegant.

b) 355 parts by weight of (E,Z)-7,8-cyclohexadecenone (composition as in Example 1.2: total perfume oil used: 1000 parts by weight) resulted in a clearly perceptible harmonisation of the composition. Additionally, (E,Z)-7,8-cyclohexadecenone produced effects that were reminiscent of musk ambrette and the composition had an elegant, exalting and crystalline musk odour. Here in particular the valuable character of (E,Z)-7,8-cyclohexadecenone was evident by comparison with compositions with conventional macrocyclic musk odorants. (E,Z)-7,8-cyclohexadecenone imparted an outstanding radiance and increased tenacity to this composition.

Examples 4 to 6

Examples of Applications

In the comparative tests described herebelow, (E,Z)-7,8-cyclohexadecenone in accordance with the invention (composition of Example 1.2) was tested in a comparison with (E,Z)-8-cyclohexadecenone which was not in accordance with the invention (composition: (E)-8-: (Z)-8-cyclohexadecenone=2:1) in personal care and washing products, both by several experts and a group of 30 lay testers (consumer test), and the essential differences in odor were determined.

Example 4

Powder Detergent 80-g portions of a powder detergent (composition: 9% C$_{12}$–C$_{13}$ linear alkylbenzene-sulphonates, 1.6% C$_{14}$–C$_{15}$ Na alkyl ethoxysulphate (EO=0.6), 5.7% C$_{12}$–C$_{18}$ alkyl sulphates, 3.3% polyacrylate (molecular weight=4,500), 27% aluminosilicate, 0.6% sodium silicate, 28% sodium carbonate, 9% sodium sulphate, 0.2% optical brighteners, 1.8% polyethylene glycol (mol. weight=4,000), 1% perborate, 1.1% enzymes (lipase, protease, cellulase), water (q.s.) were mixed with 0.2 g of a 50% solution in isopropyl myristate of (E,Z)-7,8-cyclo-hexadecenone and (E,Z)-8-cyclohexadecenone and the powder detergents were kept at room temperature for 24 hours. Thereafter two cotton towels and two mixed-fabric towels were separately machine-washed at 40° C. (manufacturer: Miele) with the 80-g portions of powder detergent.

The wet washing thereby obtained was subjected to olfactory testing and it was found that the (E,Z)-7,8-cyclohexadecenone mixture of the invention gave a markedly greater odor intensity. In addition, the crystalline nitro musk note was found to be markedly more pronounced.

Thereafter, the individual towels were line-dried for 24 hours. The perfume evaluation of both towels by an expert panel resulted in a clearly greater fragrance intensity for the (E,Z)-7,8-cyclohexadecenone mixture of the invention. In a blind evaluation, a test panel of 30 lay testers significantly preferred the towels with the (E,Z)-7,8-cyclohexadecenone mixture of the invention (p<0.05).

When the wet towels were dried in a commercial dryer, the sought-after "warm" nitro musk note was observed for the musk odorants of the invention and it resulted in a valuable harmonization, even when smaller quantities of the (E,Z)-7,8-cyclohexadecenone mixture were used.

Example 5

Fabric Softener 40-g portions of a fabric softener (triple concentrate, 94% tap water, 5.5% quaternary ethanolamine esters (ester quats, quaternary ammonium methosulphates), 0.2% alkyldimethyl-benzylammonium chloride (Preventol® R50, Bayer AG), and 0.3% of a blue dye solution) were thoroughly mixed with 0.12 g of a 50% solution in isopropyl myristate of the musk odorant mixtures (E,Z)-7,8-cyclohexadecenone, (E,Z)-8-cyclohexadecenone and 5-cyclohexadecenone (mixture of the (E) and (Z) isomers) and the softeners kept at room temperature for 24 hours. The pH of the softener concentrate was typically in the range 2–3. Thereafter, three cotton towels and three mixed-fabric towels were machine washed at 40° C. (machine manufacturer: Miele) first with 80 g of an unperfumed standard detergent powder and then separately with the fabric softeners that were to be tested.

The wet washing thereby obtained was line-dried for 24 hours. Odor evaluation of the dry towels showed that the (E,Z)-7,8-cyclohexadecenone mixture of the invention had a much greater fragrance intensity. In addition, this musk note on the towels was more persistent and more intense over a period of several days, this demonstrating its better absorptivity.

The following Table sets out the results for intensity and preference following evaluation of the dry towels after treatment with the fabric softeners using a scale of 1 (=very weak or not pleasant) to 9 (=very strong or very pleasant). In both cases, the statistical evaluation was significant (p<0.05).

| Mixture | Intensity | Preference |
|---|---|---|
| (E,Z)-7,8-Cyclohexadecenone | 4.0 | 5.9 |
| (E,Z)-8-Cyclohexadecenone | 3.1 | 5.4 |
| 5-Cyclohexadecenone | 2.9 | 5.4 |

Example 6

Shampoo 30-g portions of a shampoo (20% Plantacare® PS 10 (Cognis GmbH, Na-Laureth sulphate and lauryl glycoside), 2% sodium chloride, 1.3% citric acid, 0.5% Dragocid® Liquid (Symrise GmbH & Co. KG, mixture of phenoxyethanol, methyl, ethyl, propyl, butyl paraben), 76.2% water) were thoroughly mixed with 0.1 g of a 50% solution in isopropyl myristate of the musk odorants (E,Z)-7,8-cyclohexadecenone and (E,Z)-8-cyclohexadecenone and the shampoos kept at room temperature for 24 hours. The pH of the shampoos was about 6.

Thereafter, 20-g switches of hair (natural hair) were separately washed by hand for 1 minute, each with 1 g of each shampoo which had been worked to a lather in 2 g of water. Finally, both hair switches were separately rinsed for 30 seconds with water heated to 30° C.

The wet hair switches thereby obtained were dried for 1 minute with an electric hair dryer on a medium setting. The odor evaluation of the hair switches showed that the (E,Z)-7,8-cyclohexadecenone mixture of the invention was perceived to be more intense on both wet and dry hair and its odor was preferred.

The following Table sets outs the results for intensity and preference obtained in the evaluation of dry and wet hair switches on a scale of 1 (=very weak or not pleasant) to 9 (very strong or very pleasant). In all cases, the statistical evaluation was highly significant (p<0.01).

| Mixture | Wet hair switches | | Dry hair switches | |
|---|---|---|---|---|
| | Intensity | Preference | Intensity | Preference |
| (E,Z)-7,8-Cyclohexadecenone | 3.0 | 5.3 | 2.9 | 5.9 |
| (E,Z)-8-Cyclohexadecenone | 2.1 | 4.3 | 2.2 | 4.8 |

The invention claimed is:

1. (Z)-7-Cyclohexadecen-1-one.
2. An odorant or aroma mixture comprising (Z)-7-cyclohexadecen-1-one and one or more other odorants or aromas.
3. An odorant or aroma mixture according to claim 2 comprising (Z)-7-cyclohexadecen-1-one and (E)-7-cyclohexadecen-1-one.
4. An odorant or aroma mixture according to claim 3 wherein the weight ratio of (E)-7-cyclohexadecen-1-one to (Z)-7-cyclohexadecen-1-one is in the range from 6:1 to 1:2.
5. An odorant or aroma mixture according to claim 4 wherein the weight ratio of (E)-7 cyclohexadecen-1-one to (Z)-7-cyclohexadecen-1-one is in the range from 4:1 to 1:1.
6. An odorant or aroma mixture according to claim 3, comprising
   (Z)-7-cyclohexadecen-1-one,
   (E)-7-cyclohexadecen-1-one,
   (Z)-8-cyclohexadecen-1-one, and
   (E)-8-cyclohexadecen-1 -one.
7. An odorant or aroma mixture according to claim 6 wherein the weight ratio of (E,Z)-7-cyclohexadecen-1-one to (E,Z)-8-cyclohexadecen-1-one is in the range from 10:1 to 1:10.
8. An odorant or aroma mixture according to claim 7 wherein the weight ratio of (E,Z)-7-cyclohexadecen-1-one to (E,Z)-8-cyclohexadecen-1-one is in the range from 5:1 to 1:5.
9. An odorant or aroma mixture according to claim 8 wherein the weight ratio of (E,Z)-7-cyclohexadecen-1-one to (E,Z)-8-cyclohexadecen-1-one is in the range from 2:1 to 1:4.
10. A method for making an odorant or aroma mixture composition comprising adding (Z)-7-cyclohexadecen-1-one.
11. A method according to claim 10 comprising adding (Z)-7-cyclohexadecen-1-one in a quantity sufficient to act as a fixative.
12. A method according to claim 10 comprising adding (Z)-7-cyclohexadecen-1-one in a quantity sufficient to enhance the olfactory perception of odorants or odorant compositions.
13. A method for delivering, enhancing or modifying a musk odour comprising adding to a product to be scented a sensorily-active quantity of (Z)-7-cyclohexadecen-1-one.
14. A perfumed product comprising (Z)-7-cyclohexadecen-1-one.
15. A perfumed product according to claim 14 wherein the product is a detergent, toiletry or personal care formulation.
16. A method for the preparation of (E/Z)-7-cyclohexadecen-1-one having the following steps:
   (a) partially reducing 1,8-cyclohexadecanedione to the corresponding hydroxyketone, and
   (b) dehydrating the hydroxyketone to (E/Z)-7-cyclohexadecen-1-one.

* * * * *

UNITED STATES PATENT AND TRADEMARK OFFICE
CERTIFICATE OF CORRECTION

PATENT NO. : 7,129,380 B2
APPLICATION NO. : 11/016896
DATED : October 31, 2006
INVENTOR(S) : Aurelia Reckziegel et al.

It is certified that error appears in the above-identified patent and that said Letters Patent is hereby corrected as shown below:

Col. 5, line, 27 change "(E)-8-cyclohexadecen-1-one, the weight ratio of (E,Z)-" to
--(E)-8-cyclohexadecen-1-one,--

Col. 5, line, 28 start a new line with a text to the margin, add the text
--the weight ratio of (E,Z)- --

The remaining existing text of Col. 5 lines 28,29,30 and 31 should follow the new line at Col. 5, line, 28, and should not be indented and should be at the margin.

Col. 6, line 49 change "catalyst from the group VII" to

--catalyst from the group VIII--

CLAIMS:

Col. 22, line 20 change "ratio of(E)-7-cyclohexadecen-1-one" to

--ratio of (E)-7-cyclohexadecen-1-one--

Col. 22, line 23 change "ratio of(E)-7-cyclohexadecen-1-one" to

--ratio of (E)-7-cyclohexadecen-1-one--

Col. 22, line 32 change "ratio of(E,Z)-7-cycloheadecen-1-one" to

--ratio of (E,Z)-7-cycloheadecen-1-one--

Col. 22, line 36 change "ratio of(E,Z)-7-cycloheadecen-1-one" to

--ratio of (E,Z)-7-cycloheadecen-1-one--

UNITED STATES PATENT AND TRADEMARK OFFICE
CERTIFICATE OF CORRECTION

PATENT NO.        : 7,129,380 B2
APPLICATION NO.   : 11/016896
DATED             : October 31, 2006
INVENTOR(S)       : Aurelia Reckziegel et al.

It is certified that error appears in the above-identified patent and that said Letters Patent is hereby corrected as shown below:

Col. 22, line 60 change "(E,Z)-7-cvclohexadecen-1-one" to

--(E,Z)-7-cyclohexadecen-1-one--

Signed and Sealed this

Twentieth Day of February, 2007

JON W. DUDAS
*Director of the United States Patent and Trademark Office*